United States Patent
Duke et al.

(10) Patent No.: US 8,725,530 B2
(45) Date of Patent: May 13, 2014

(54) SYSTEMS, METHODS, AND APPARATUS FOR USE IN GATHERING AND PROVIDING HEALTHCARE INFORMATION

(75) Inventors: David O. Duke, Arroyo Grande, CA (US); Janet K. Duke, Arroyo Grande, CA (US); Linda Byron-Alton, San Luis Obispo, CA (US); Joe Cockrill Jauregui, Charlotte, NC (US)

(73) Assignee: Mastodon, LLC, Charlotte, NC (US)

( * ) Notice: Subject to any disclaimer, the term of this patent is extended or adjusted under 35 U.S.C. 154(b) by 0 days.

(21) Appl. No.: 13/113,845

(22) Filed: May 23, 2011

(65) Prior Publication Data

US 2011/0288887 A1    Nov. 24, 2011

Related U.S. Application Data

(63) Continuation-in-part of application No. 12/329,754, filed on Dec. 8, 2008, now abandoned, and a continuation-in-part of application No. 12/371,033, filed on Feb. 13, 2009, now abandoned.

(51) Int. Cl.
     *G06Q 50/00*      (2012.01)
     *G06Q 10/00*      (2012.01)

(52) U.S. Cl.
     USPC .................................. 705/2; 705/3

(58) Field of Classification Search
     USPC ............................................ 705/2
     See application file for complete search history.

(56) References Cited

U.S. PATENT DOCUMENTS

| | | | |
|---|---|---|---|
| 4,643,205 A | 2/1987 | Redding et al. | |
| 4,796,181 A | 1/1989 | Wiedemer | |
| 5,583,758 A | 12/1996 | McIlroy et al. | |
| 5,832,448 A | 11/1998 | Brown | |
| 5,918,603 A * | 7/1999 | Brown .......................... | 128/897 |
| 5,933,136 A | 8/1999 | Brown | |
| 5,967,789 A | 10/1999 | Segel et al. | |
| 6,018,713 A | 1/2000 | Coli et al. | |
| 6,294,999 B1 | 9/2001 | Yarin et al. | |
| 6,826,536 B1 | 11/2004 | Forman | |
| 2002/0022973 A1 | 2/2002 | Sun et al. | |
| 2002/0082863 A1 | 6/2002 | Kleinke | |
| 2002/0184050 A1 * | 12/2002 | Papageorge ...................... | 705/2 |
| 2003/0028482 A1 | 2/2003 | Burak et al. | |

(Continued)

OTHER PUBLICATIONS

Brennan, Improving Health Care by Understanding Patient Preferences: The Role of Computer Technology, Journal of the American Medical Informatics Association, vol. 5, No. 3, May/Jun. 1998, 6 pages.*

(Continued)

*Primary Examiner* — Tran Nguyen
(74) *Attorney, Agent, or Firm* — Tillman Wright, PLLC; Chad D. Tillman; Jeremy C. Doerre

(57) ABSTRACT

A method for presenting a favored treatment includes querying, via an electronic device, a patient regarding a healthcare issue; providing, to the patient via the electronic device, information regarding a favored treatment for the healthcare issue; receiving, from the patient via the electronic device, an indication of a preferred treatment; and effecting printing of a document based on information input by the patient via the electronic device. The document includes an identification of the preferred treatment of the patient.

20 Claims, 23 Drawing Sheets

(56) References Cited

U.S. PATENT DOCUMENTS

| | | |
|---|---|---|
| 2003/0036683 A1* | 2/2003 | Kehr et al. .................... 600/300 |
| 2003/0139942 A1* | 7/2003 | Rakshit et al. ................... 705/1 |
| 2004/0260577 A1 | 12/2004 | Dahlin et al. |
| 2006/0026051 A1* | 2/2006 | Rose ................................ 705/8 |
| 2007/0250341 A1* | 10/2007 | Howe et al. ....................... 705/2 |
| 2008/0059230 A1 | 3/2008 | Manning |
| 2008/0091592 A1* | 4/2008 | Blackburn et al. .............. 705/38 |

OTHER PUBLICATIONS

Ingram, Trinity L., Compliance: A Concept Analysis, Nursing Forum, Jul.-Sep. 2009, http://findarticles.com/p/articles/mi_7680/is_200907/ai_n42041393/, 12 pages.

National Cancer Institute, Handheld Computer Smoking Intervention Tool (HCSIT) 2.0 Palm Version Manual, 2002 University of Virginia Patent Foundation, 2005 UVA Patent Foundation, US, 13 pages.

* cited by examiner

Advertisement
Start / End    Questions? Need Help?
               Tap Here.
Welcome!
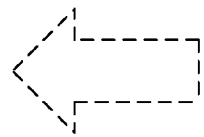
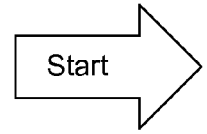
DirectPoint
*FIG. 1*

FIG. 4

Advertisement

Start / End        Questions? Need Help?
                   Tap Here.

Your record shows that you've had:
CHF, Cigarette use, and Back Pain.

In order to best let your doctor know what is affecting your health now, it is important to know any additional issues you've had in the past.

☐ Depression, anxiety, or psychiatric history      ☐ Anemia

☐ Impaired kidney function      ☐ Seizures

☐ Irregular heart rhythm      ☐ Pancreatitis

Check all boxes that apply.

⇐ Back        DirectPoint        Next ⇒

FIG. 7

Advertisement

Start / End        Questions? Need Help?
                   Tap Here.

Your record shows that you take the following medications:
Aspirin, Lisinopril, and Crestor.

To help your doctor know the best medication to prescribe for you, it's important to know if you take any of the following:

☐ Nicotine replacement            ☐ Diabetic medications

☐ Tikosyn / Dofetilide            ☐ Anti-epileptic medications

☐ Buprorion / Wellbutrin / Zyban  ☐ Migraine medications

☐ Contraception / Birth Control   ☐ Herbal / Holistic meds

☐ Over the counter medications    ☐ Other

Check all boxes that apply.

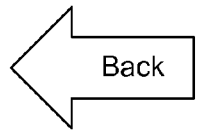 Back           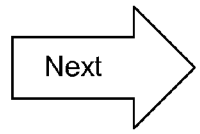 Next

DirectPoint

*FIG. 8*

Advertisement

Start / End    Questions? Need Help?
                     Tap Here.

In order to let your doctor know what might affect you in the future, it helps to know what issue those related to you (Mom, Dad, Brothers, Sisters, Children) have had:

- ☐ Depression, anxiety, or psychiatric history
- ☐ Impaired kidney function
- ☐ Irregular heart rhythm
- ☐ Anemia
- ☐ Seizures
- ☐ Pancreatitis Check all boxes that apply.

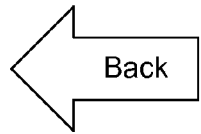 Back         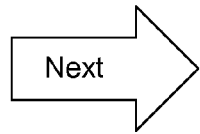 Next

DirectPoint

*FIG. 9*

```
                    Advertisement
Start / End          Questions? Need Help?
                         Tap Here.
          What type of surgeries have you had in the past?
    ☐   Head / Throat / Eye        ☐   Abdominal / Stomach
    ☐   Back / Neck / Spine        ☐   Back / Neck / Spine
    ☐   Chest / Lungs / Heart      ☐   Orthopedic
    ☐   Female                     ☐   Other
                    Check all boxes that apply.
```
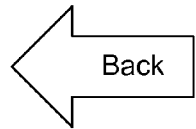
Back
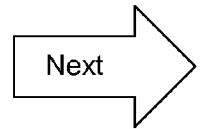
Next
DirectPoint
FIG. 10

Advertisement

Start / End    Questions? Need Help?
               Tap Here.

What social habits do you have?

☐ Tobacco / Smoking      ☐ Prescription medication
                            for non-prescribed use
☐ Alcohol                ☐ Other
☐ Recreational Drugs     ☐ Changing work shifts
                            and/or insomnia Check all boxes that apply.

⬅ Back         DirectPoint         Next ➡

FIG. 12

Advertisement

Start / End          Questions? Need Help?
                         Tap Here.

1. How many cigarettes do you smoke daily?

☐ <1          ☐ 3-5          ☐ > 1 pack

☐ 1-2         ☐ 1 pack       ☐ I don't currently smoke

2. Do you use any other tobacco products?

☐ Pipe        ☐ Cigars       ☐ No

☐ Snuff       ☐ Chewing tobacco

If so, how many times a day?

☐ <1          ☐ 3-5

☐ 1-2         ☐ >5

3. Does anyone you live with smoke?

☐ Yes         ☐ No

Check all boxes that apply.

⬅ Back                              Next ➡

DirectPoint

*FIG. 14*

Advertisement

Start / End          Questions? Need Help?
                     Tap Here.

4. When you wake up, how soon do you smoke your first cigarette?
- [ ] < 5 mins
- [ ] 31-60 mins
- [ ] 6-30 mins
- [ ] > 60 mins 5. How interested are you in stopping your tobacco use?
- [ ] Not at all
- [ ] Moderately
- [ ] A little
- [ ] Very 6. Do you seriously intend to stop in the next month?
- [ ] Yes
- [ ] No 7. If you decided to stop during the next two weeks, how confident are you that you would succeed?
- [ ] Not at all
- [ ] Moderately
- [ ] A little
- [ ] Very Check all boxes that apply.

⬅ Back          DirectPoint          Next ➡

*FIG. 15*

Advertisement

Start / End       Questions? Need Help?
                  Tap Here.

Drug X may not be appropriate for me if I have suffered from:
(Check all boxes that apply to your health history)

☐ Depression, anxiety, or psychiatric history      ☐ Anemia

☐ Impaired kidney function      ☐ Seizures

☐ Irregular heart rhythm      ☐ Pancreatitis

I have reviewed the contraindications above
and checked the appropriate boxes.

| Replay Video | Back |

DirectPoint

*FIG. 17*

Advertisement

Start / End       Questions? Need Help?
                  Tap Here.

Depending on your situation, your insurance may cover or partially cover Drug X:

Check all boxes that apply.

Single ☐    Married ☐    Live in US ☐

Have prescription drug benefit coverage? ☐

Number of persons in your household? ☐ △▽

Household income:

☐ Less than $19,000          ☐ $28,001 to $35,200
☐ $19,601 to $26,400         ☐ $35,201 to $42,400
☐ $26,401 to $28,000         ☐ More than $42,400

**Congratulations!
You've finished.**

⇐ Back                              End ⇒

DirectPoint

*FIG. 19*

SYSTEMS, METHODS, AND APPARATUS FOR USE IN GATHERING AND PROVIDING HEALTHCARE INFORMATION

CROSS-REFERENCE TO RELATED APPLICATION

The present application is a U.S. continuation-in-part patent application of, and claims priority under 35 U.S.C. §120 to,
(a) U.S. nonprovisional patent application Ser. No. 12/329,754, filed Dec. 8, 2008 now abandoned, which nonprovisional patent application published as U.S. patent application publication no. 2010/0145726, and
(a) U.S. nonprovisional patent application Ser. No. 12/371,033, filed Feb. 13, 2009 now abandoned, which nonprovisional patent application published as U.S. patent application publication no. 2010/0211407,
which patent applications and any patent application publications thereof are hereby incorporated herein by reference.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to systems, methods, and apparatus for use in gathering and providing information in a healthcare context. Traditionally, when a patient visits a healthcare service provider, he or she checks in and receives a clipboard with several printouts to fill out. Although computing devices are widely used in many contexts today, widespread use of computing devices for data gathering in a healthcare service provider context is believed to be cost prohibitive.

A need exists for improvement in systems, methods, and apparatus for use in gathering and providing information in a healthcare context. This, and other needs, are addressed by one or more aspects of the present invention.

SUMMARY OF THE INVENTION

The present invention includes many aspects and features. Moreover, while many aspects and features relate to, and are described in, the context of a health care environment, the present invention is not limited to use only in this context, as will become apparent from the following summaries and detailed descriptions of aspects, features, and one or more embodiments of the present invention.

Accordingly, one aspect of the present invention relates to a method for presenting a favored treatment. The method includes querying, via an electronic device, a patient regarding a healthcare issue; providing, to the patient via the electronic device, information regarding a favored treatment for the healthcare issue; receiving, from the patient via the electronic device, an indication of a preferred treatment; and effecting printing of a document based on information input by the patient via the electronic device. The document includes an identification of the preferred treatment of the patient.

In a feature of this aspect, the preferred treatment of the patient is the favored treatment.

In a feature of this aspect, the method further comprises a step of effecting printing of a prescription for the preferred treatment of the patient.

In a feature of this aspect, the step of providing, to the patient via the electronic device, information regarding a favored treatment for the healthcare issue comprises presenting a video to the patient via the electronic device.

In a feature of this aspect, the method further comprises a step of presenting, to the patient via the electronic device, other treatments.

In a feature of this aspect, the preferred treatment of the patient is not the favored treatment, and wherein the document includes an identification of the favored treatment. In one or more implementations, the document further includes information regarding one or more disadvantages of the preferred treatment of the patient. In some implementations, the one or more disadvantages are identified based at least in part on information input by the patient via the electronic device. In one or more implementations, the document further includes information regarding one or more advantages of the favored treatment.

In a feature of this aspect, the method further comprises steps of querying, via the electronic device, a patient regarding information for calculating third party benefit information; determining third party benefit information for the patient; and presenting determined third party benefit information to the patient.

In a feature of this aspect, the document includes information regarding counseling for the healthcare issue.

In a feature of this aspect, the document includes information regarding billing for counseling for the healthcare issue.

In a feature of this aspect, the document comprises a checklist including information regarding counseling for the healthcare issue.

In a feature of this aspect, the document includes an indication of an amount of time to spend discussing a certain healthcare issue with the patient.

In a feature of this aspect, the document is configured for use in billing.

In a feature of this aspect, the method further includes a step of updating a medical record of the patient based on information input by the patient via the electronic device.

Another aspect of the present invention relates to a system for a healthcare environment comprising one or more electronic devices disposed in a healthcare environment, each electronic device including software loaded thereon configured to allow a user to input information associated with a visit to a healthcare service provider, and present to a user a favored treatment in response to information input by a user indicating the existence of a particular healthcare issue. The system further includes a base station configured to receive information from the one or more electronic devices, and effect printing of a document based on information received from the one or more electronic devices.

In a feature of this aspect, the base station is configured to effect printing of a prescription based on information received from the one or more electronic devices.

Another aspect of the present invention relates to a method for advertising a treatment. The method includes configuring, by a party, one or more electronic devices for use in electronic check in in a healthcare environment, the configuring including configuring the devices to favor a treatment associated with the party and to present information associated with such favored treatment to a user in response to an indication of a particular healthcare condition; and providing the one or more electronic devices to a second party, the second party being a healthcare service provider.

In a feature of this aspect, the favored treatment is a drug.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein:

FIG. 1 illustrates a start screen for exemplary software loaded on an electronic device.

FIG. 4 illustrates a birth date input screen for the exemplary software of FIG. 1;

FIG. 7 illustrates an exemplary screen querying a user regarding past healthcare issues;

FIG. 8 illustrates an exemplary screen querying a user regarding current medications;

FIG. 9 illustrates an exemplary screen querying a user regarding his or her family medical history;

FIG. 10 illustrates an exemplary screen querying a user regarding past surgical procedures;

FIGS. 12-15 illustrate exemplary screens querying a user regarding social habits;

FIG. 17 illustrates an exemplary screen querying a user regarding contraindications of a treatment;

FIG. 19 illustrates an exemplary screen querying a user regarding information for determining third party benefit information;

DETAILED DESCRIPTION

Figure 2:
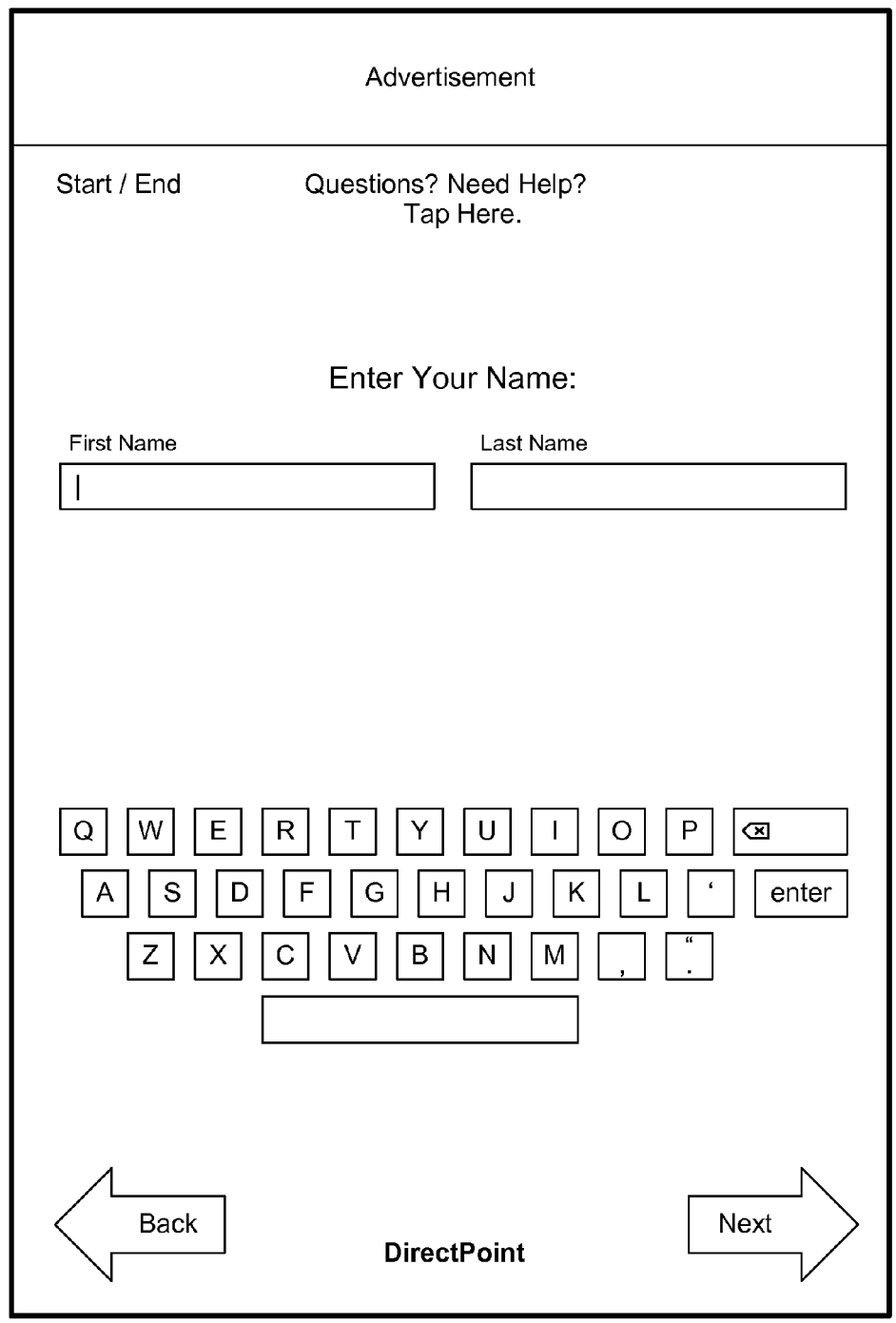
FIG. 2 illustrates a name input screen for the exemplary software of FIG. 1.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. §112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

Exemplary Electronic Devices

In accordance with one or more preferred embodiments, an electronic device is utilized in a healthcare environment to capture data from a user, such as a patient or healthcare worker (who may be, for example, assisting a patient in inputting data). Preferably, this device includes a touchscreen display, although, in at least some implementations, input may be provided via alternative, or additional, means, such as, for example, a keyboard, mouse, touchpad, or buttons. In some preferred implementations, the electronic device comprises a tablet (e.g. an iPad), smartphone, PDA, laptop, personal computer, or other electronic device.

The electronic device preferably includes software loaded thereon configured to query a user for information, such as, for example, biographical information, contact information, information regarding the reason for a medical visit, personal medical history information, family medical history information, allergy information, insurance information, financial information, and personal habit information.

In one or more preferred implementations, such an electronic device is provided to a patient upon arriving at a healthcare environment. In some implementations, such an electronic device is provided to all patients who seek healthcare services at the healthcare environment, while in at least some other implementations patients are queried (e.g. by a healthcare worker) regarding one or more healthcare issues and only provided with an electronic device if they suffer from one or more healthcare issues for which a treatment option (as described in more detail hereinbelow) is available.

Exemplary Software

FIG. 1 illustrates a start screen for exemplary software loaded on an electronic device. The software is configured to run on an electronic device having a touchscreen. The start screen represents a preferred starting point for a user's interaction with the software.

Preferably, the software is configured to present advertising to a user of the electronic device, as illustrated in FIG. 1. In some preferred implementations, at least some of the advertising represents targeted advertising. Such targeted advertising may be targeted based on, for example, information provided by a user of an electronic device, an identity of a healthcare provider associated with the electronic device, or information associated with a user of the electronic device.

Figure 3:
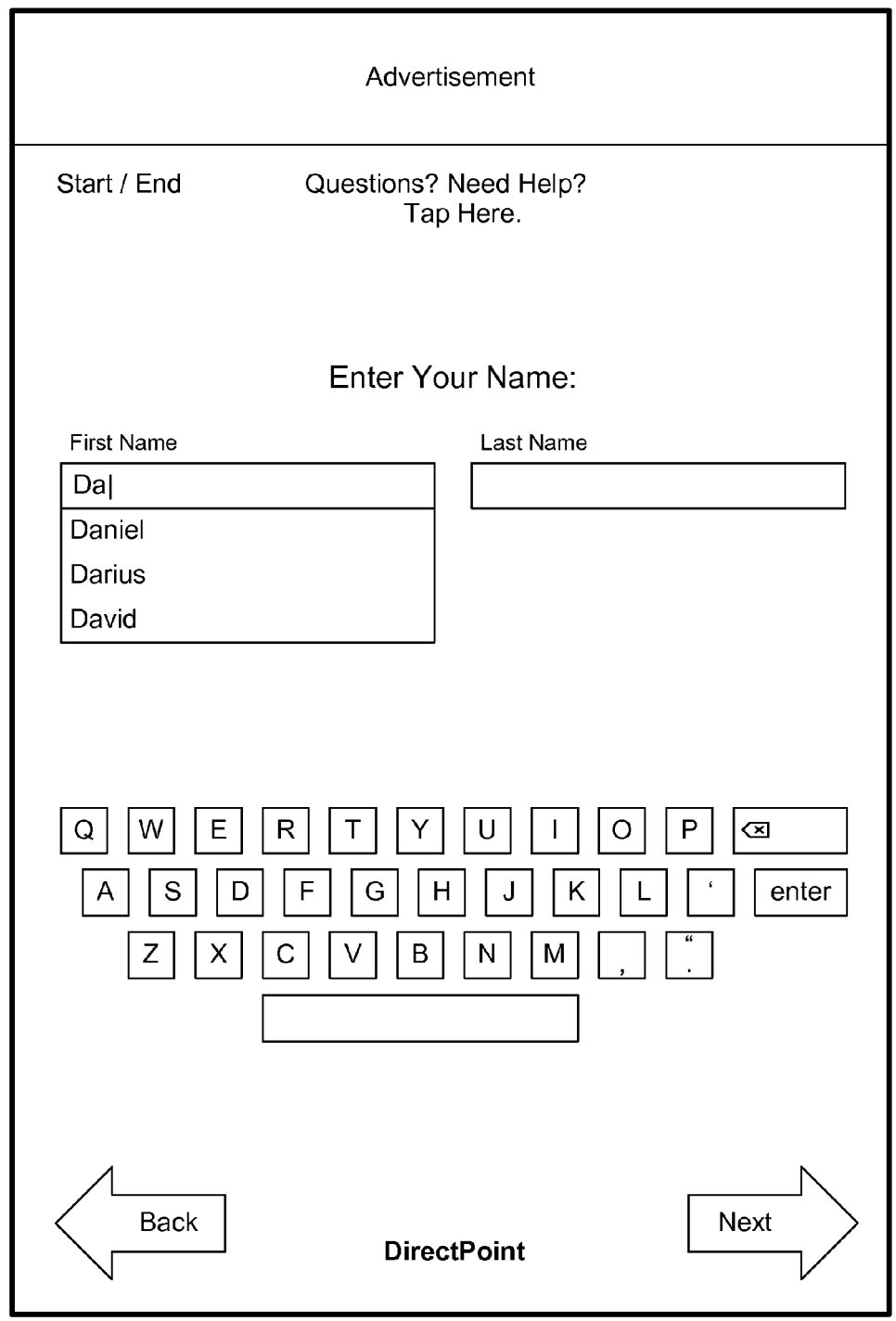
FIG. 3 illustrates use of a suggestion box in the exemplary software of FIG. 1.

From the start screen, a user proceeds via a start button, which is illustrated in FIG. 1. Thereafter, the user is presented with a name input screen, as illustrated in FIG. 2. The name input screen allows a user to input his or her name using a displayed keyboard. In some preferred implementations, when a user begins entering his or her name, a suggestion box pops up to display suggestions that the user can select, as illustrated in FIG. 3. In some preferred implementations, such suggestions are based on data regarding common names, while in at least some other implementations such suggestions are based on patient data, or even on data for patients who have an appointment scheduled (e.g. patients who have an appointment scheduled for the current day, or the current week).

Figure 4:
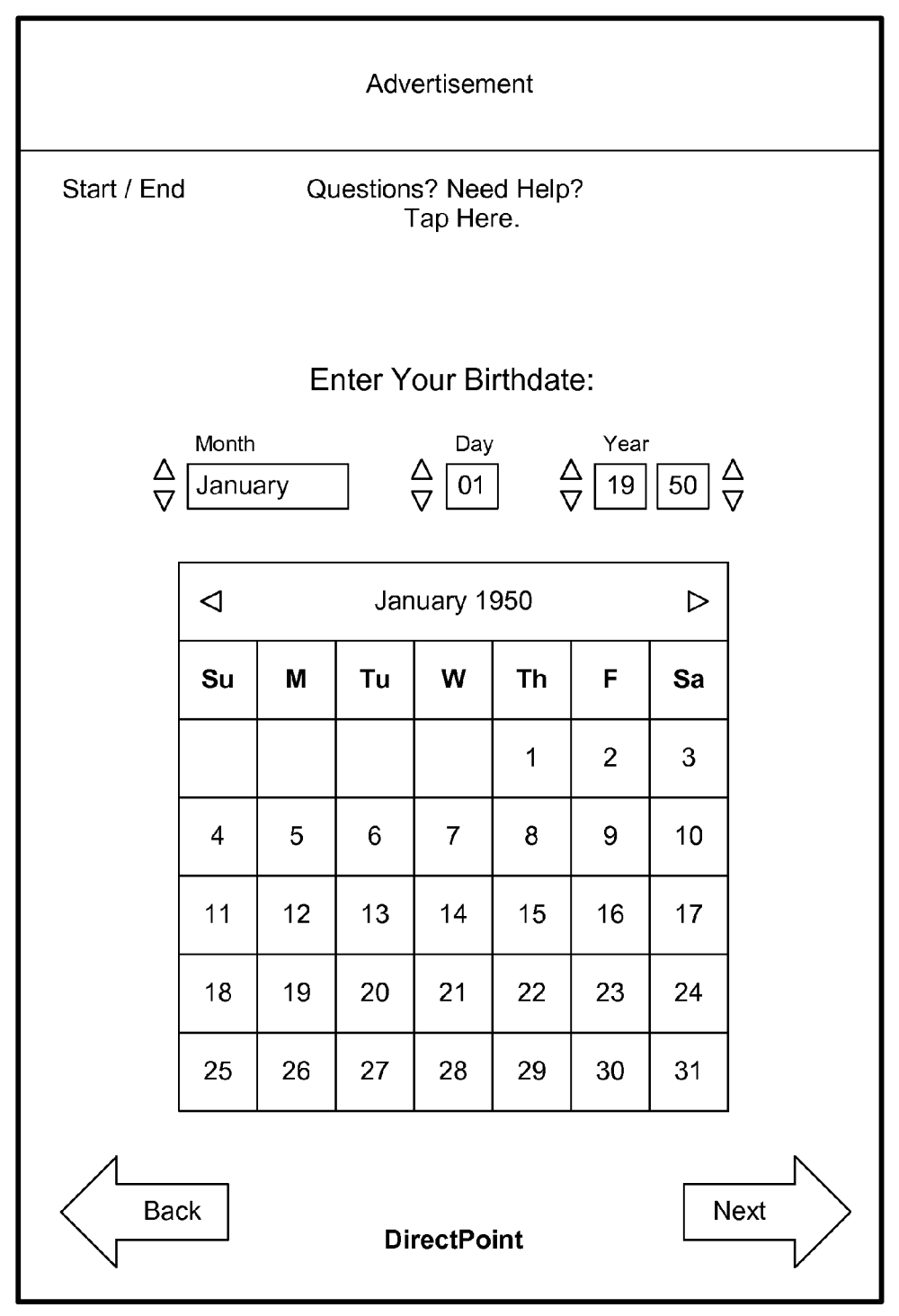
Figure 5:
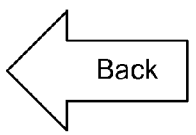
FIG. 5 illustrates an address input screen for the exemplary software of FIG. 1.

After entering their name, a user proceeds through additional screens configured to prompt a user to input additional biographical information, such as, for example, a birth date as illustrated in FIG. 4, and an address as illustrated in FIG. 5.

Figure 6:
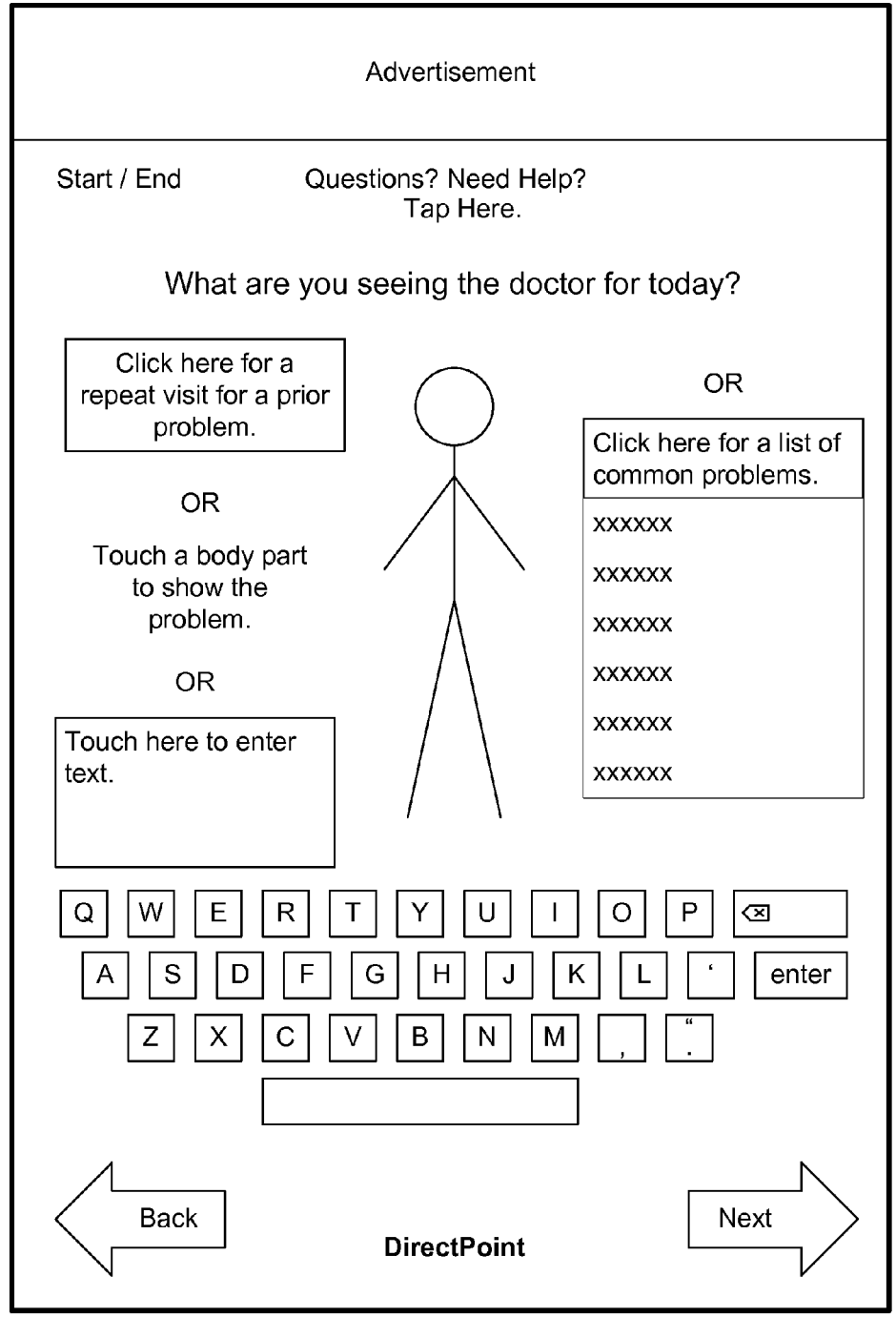
FIG. 6 illustrates an exemplary screen querying a user regarding a reason for his or her visit to a healthcare provider.

Following entry of such biographical information, the software preferably presents to a user one or more screens querying the user regarding one or more specific healthcare problems. For example, the software preferably includes a screen querying a user regarding the reason for his or her visit to a healthcare provider, as illustrated in FIG. 6. In some preferred implementations, the software is configured to review, access, scan, or otherwise look up healthcare information pertaining to a user (or patient), present such information to a user for confirmation, and determine additional inquiries or present additional information based on such healthcare information.

For example, the software is preferably configured to present a list of known past healthcare issues to a user, and query the user regarding additional healthcare issues, as illustrated in FIG. 7. The list of additional healthcare issues that a user is queried regarding may be based on health information of the user, biographical information of the user, other information of the user, or may be selected based on being contraindications for a particular treatment, drug, or product.

Similarly, the software is preferably configured to present a list of known current medications to a user, and query the user regarding additional current medications, as illustrated in FIG. 8. The list of additional current medications that a user is queried regarding may be based on health information of the user, biographical information of the user, other information of the user, or may be selected based on the existence of potential side effects when used in combination with a particular treatment, drug, or product.

In at least some preferred implementations, the software is programmed to help a user recall medication a patient has taken or is taking. For example, if a user indicates the use of heart medication, a user could be prompted to identify its color, shape, or size, and could even be provided answer choices such as "a little white pill for my heart". An iterative process could be utilized to narrow down a medication to one or more possibilities. For example, a user could be queried as to a frequency a medication is taken, and even shown pictures of potential medications matching the provided information.

Figure 11:
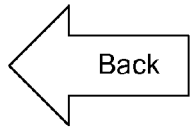
FIG. 11 illustrates an exemplary screen querying a user regarding allergies.
Figure 13:
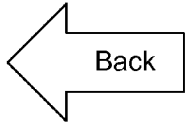

Additionally, the software is preferably configured to query a user regarding healthcare issues suffered by family members, as illustrated in FIG. 9, past surgeries, as illustrated in FIG. 10, allergies, as illustrated in FIG. 11, and social habits, as illustrated in FIG. 12. In one or more preferred implementations, the software is configured to query a user in additional detail regarding a selection made on one or more of these pages, as illustrated in FIGS. 13-15.

Figure 16:
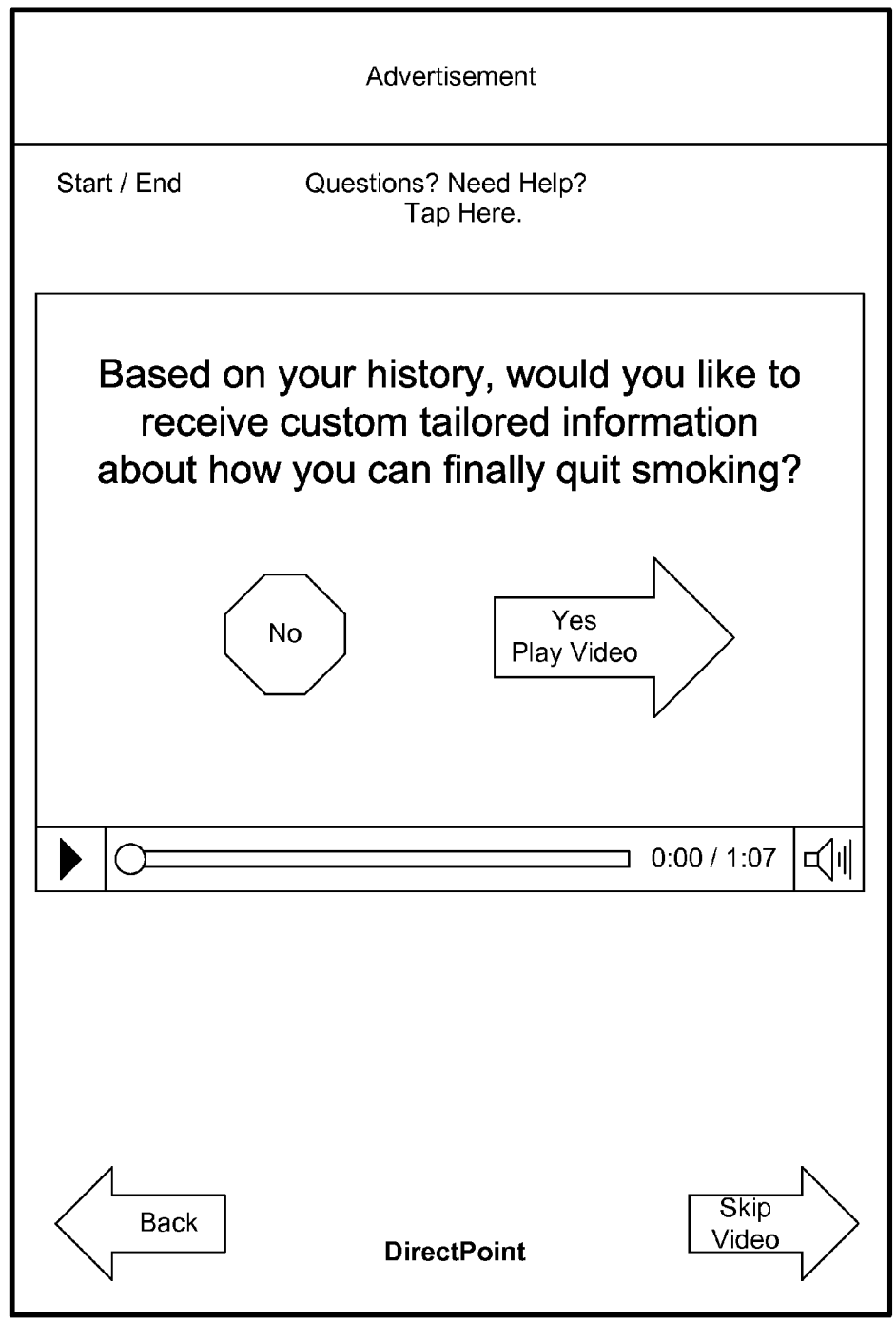
FIG. 16 illustrates an exemplary screen presenting a video for viewing by a user.

In some preferred implementations, the software is configured to identify a healthcare issue of a user for which one or more treatment options are available, and present information to a user regarding the healthcare issue and/or the one or more available treatment options. Such identified treatment options may include a specific product, drug, or treatment, and such presented information may include an informative video, as illustrated in FIG. 16.

Figure 18:
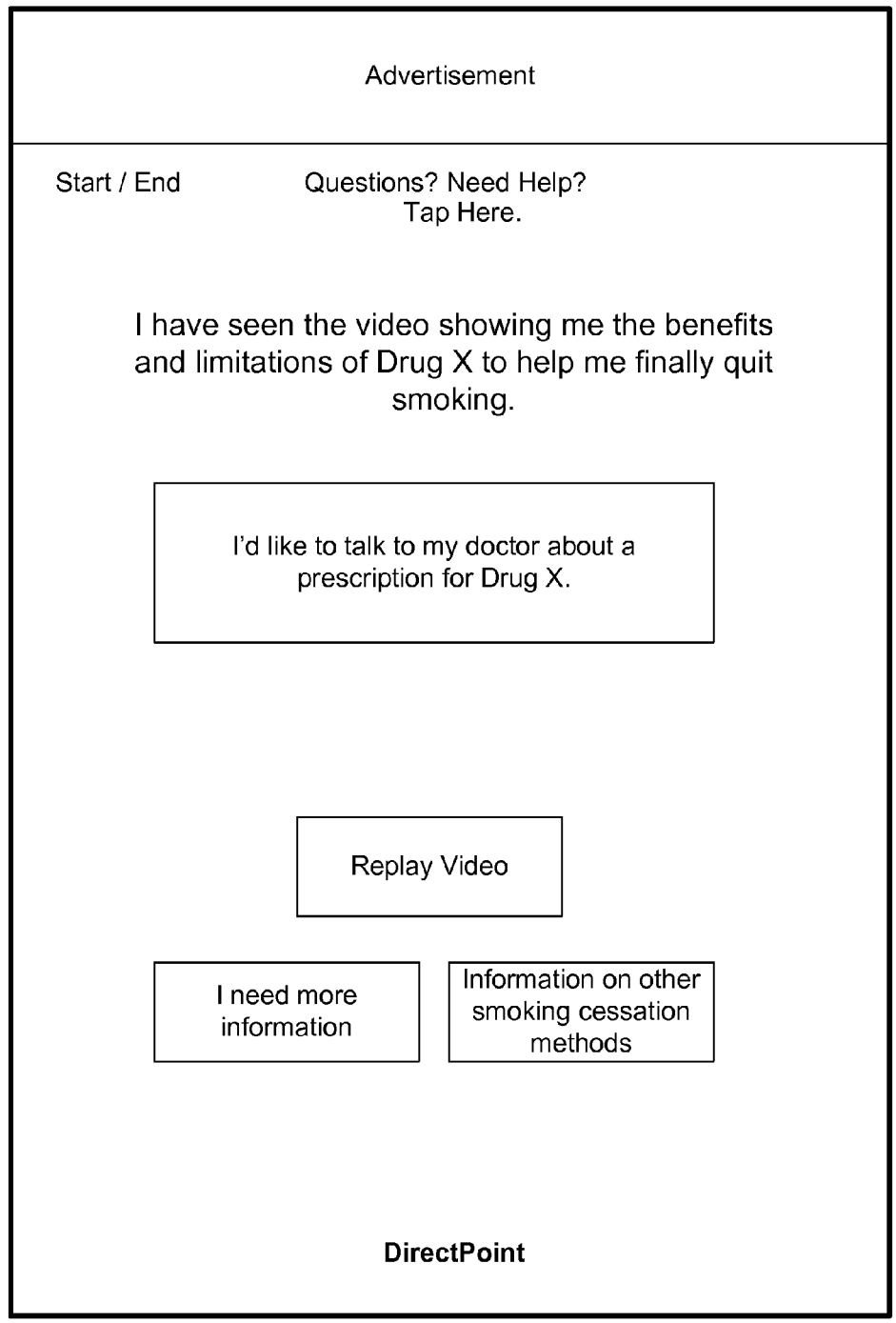
FIG. 18 illustrates an exemplary screen querying a user regarding their interest in a treatment.

Preferably, if a specific product, drug, or treatment is identified, the user is presented with a list of contraindications for that specific product, drug, or treatment, and instructed to confirm whether any are applicable to them, as illustrated in FIG. 17. The software preferably presents the user with the option of indicating that they would like to talk to their doctor about a treatment option that has been presented to them, as illustrated in FIG. 18. The software additionally preferably presents a user with the option to review additional information regarding an identified treatment option, or other, alternative, treatment options, as also illustrated in FIG. 18.

In some preferred implementations, if a user indicates that they would like to talk to their doctor about a specific treatment option, the software preferably queries the user regarding information associated with, or effecting, third party coverage of treatment costs, such as, for example, residence information, insurance information, marital status, and annual income, as illustrated in FIG. 19. Such third party coverage information may include, for example, information associated with an insurance company (such as Blue Cross Blue Shield), information associated with a club, group, or association (such as the Association for the Advancement of Retired Persons), or information associated with a rewards card.

Figure 20:
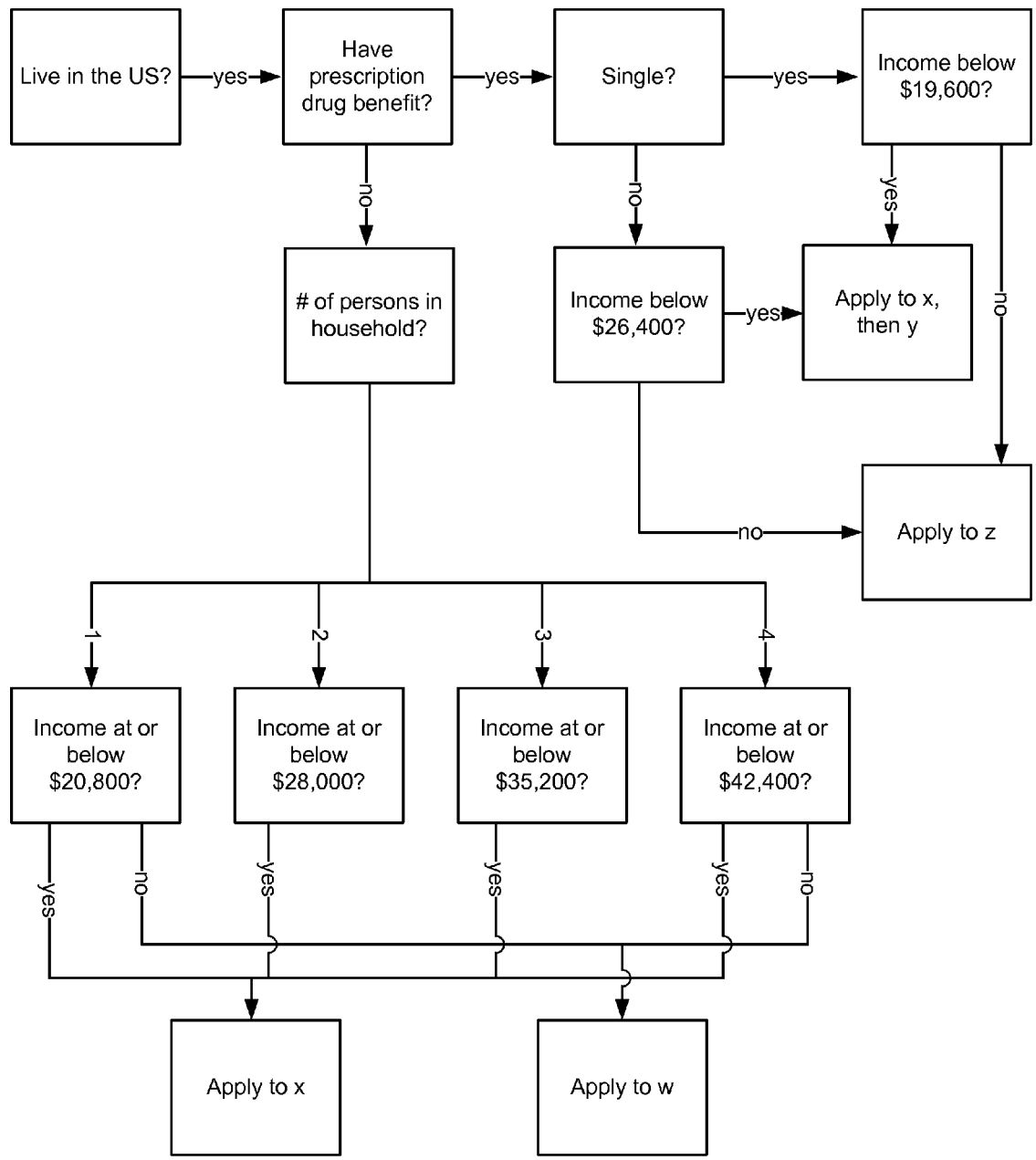
FIG. 20 illustrates an exemplary algorithm for determining third party benefit information.

Preferably, software at the electronic device is configured to calculate third party coverage information based on patient information (which may be user provided or may be retrieved). FIG. 20 illustrates an exemplary algorithm for determining potential third party coverage based on information provided via the screen of FIG. 19. This algorithm generates a recommendation as to where to apply for potential third party coverage of a treatment option. In some preferred implementations, such a recommendation is presented to the user via the software.

In one or more preferred implementations, the software is configured to determine requirements for third party reimbursement, payment, or coverage, such as, for example, Medicaid requirements, Medicare requirements, requirements set forth by the Patient Protection and Affordable Care Act (PPACA), other reimbursement regime requirements, or third party benefits requirements for payment. Such determination may be made utilizing data stored on an electronic device the software is loaded on, and/or may be made utilizing data accessed from a remote server, database, or from another remote location. In at least some preferred implementations, such a determination is made at another remote device, such as, for example, a base station configured for use with one or more electronic devices having software loaded thereon as described hereinabove. In some preferred implementations, a determination made by another remote device is communicated back to a first electronic device for presentation to a user.

In some preferred implementations, the software is configured to, upon a determination that a particular product is not eligible for third party coverage or reimbursement, merely present advertising content to a user regarding the product, or, alternatively, redirect the user to a screen or webpage for ordering of the product. For example, in some preferred implementations, the software redirects a user to target.com, cvs.com, or amazon.com for ordering of an over the counter medication. Alternatively, the software is configured to directly allow a user to order a product.

Exemplary System

Exemplary software for an electronic device for use by a patient or other user in a healthcare environment has been described hereinabove. In some preferred implementations, one or more such electronic devices are utilized in a system configured for use in a healthcare environment. Further, although described hereinabove in the context of software for use on a device in a healthcare environment, similar software could equally be utilized on a computing device disposed remotely from a health care environment. In one or more preferred implementations, the system is configured for use with computing devices having such software loaded thereon, such as, for example, a user's home computer.

The system preferably allows information collected via the one or more electronic devices over a physical connection or over a wireless connection, or via one or more computing devices over a network such as the internet, to be electronically stored, printed, and/or communicated to a healthcare provider. For example, an electronic device could engage in wireless or wired communication with a printer to effect such printing, or could engage in wireless or wired communications with a base station which in turn effects printing.

In some preferred implementations, such information is utilized to update one or more medical records databases.

Additionally, in some preferred implementations, such information is printed on one or more pages for use by a healthcare provider, or is communicated to another electronic device for printing and/or electronic storage, or is communicated to another electronic device for display and viewing by one or more healthcare professionals.

In a preferred implementation, the software is configured to effect printing of, or communicate to another device for printing of, a checklist for use by a healthcare provider, a billing capture sticker, and a pre-printed prescription. In some preferred implementations, the software is further configured to effect generation of, and printing or electronic storage of, documentation required for third party coverage, reimbursement, or payment.

In some preferred implementations, the checklist is generated based on determined reimbursement, payment, or coverage requirements, as described hereinabove.

For example, in an exemplary use case, a patient indicates via software loaded on an electronic device that they are over 65, currently smoke, are interested in quitting, and are interested in talking to a doctor about Drug X as a treatment option. Preferably, based on this, software, either loaded on the electronic device utilized by the patient, or loaded on another electronic device, looks up Medicare reimbursement information for smoking and tobacco use counseling, and determines that more than three minutes of smoking and tobacco use counseling must be provided for a first reimbursement amount, and that more than ten minutes of smoking and tobacco use counseling must be provided for a second reimbursement amount. Preferably, a checklist is generated that indicates this to a healthcare provider who sees the patient, thereby informing the healthcare provider how long they need to spend on smoking and tobacco use counseling in order to qualify for certain reimbursement amounts. In some preferred implementations, such a checklist further provides informative checklist points to a healthcare provider to utilize during their smoking and tobacco use counseling with the patient. Further still, in at least some preferred implementations, such a checklist suggests one or more diagnoses for the visit which are appropriate for the patient's counseling, such as, for example, emphysema.

The provision of such a checklist is believed to allow the healthcare provider to more efficiently manage time spent with the patient.

Preferably, if a patient previously expressed a preference for a particular treatment option during interaction with software loaded on an electronic device, that preference is included on the checklist. As noted above, in some implementations, a prescription for a treatment option may already have been printed, alternatively, however, the checklist may include a checkbox indicating that the healthcare provider would like a prescription for such treatment option to be printed.

In some implementations, if a patient previously expressed a preference for a particular treatment option, but another treatment option is determined by software, either loaded on an electronic device utilized by the patient, or on another electronic device, to be a potentially superior treatment option, this information is presented on such a checklist together with the reasoning for such determination. For example, a checklist might include language that although a patient expressed a preference for Drug Y, there may be complications, or contraindications, and that another drug, Drug X, includes no contraindications and has additional benefits.

Additionally or alternatively, in at least some implementations, even if a patient previously expressed a preference for a particular treatment option, if another treatment option is determined to be potentially applicable, and is favored or preferred for commercial or other reasons, such favored treatment is preferably presented via the checklist together with any potential benefits, and any potential downsides associated with a treatment option for which the patient expressed a preference.

In some preferred implementations, this is believed to provide two chances for selection of a favored treatment option. First, a patient is provided the opportunity to select a favored treatment option via software loaded on an electronic device, and, second, even if the patient does not select the favored treatment option, a healthcare provider is provided the opportunity to select the favored treatment option when it is presented on the checklist.

In some preferred implementations, a checklist that has been generated and printed as described hereinabove, and then is utilized by a healthcare provider while seeing a patient, can thereafter serve as a billing capture sticker which provides information facilitating the billing process.

In a preferred implementation, a healthcare provider is able to effect configuration changes so as to customize the screens and options presented to a user via software loaded on an electronic device as described hereinabove.

For example, in an exemplary use case, a healthcare provider effects changes so that Drug X is never suggested, but Drug Z is suggested to a user when certain preconditions are met.

Preferably, software loaded on an electronic device allows a healthcare provider to readily and easily effect such changes. Such software may be the same software as that utilized by a patient for entering information, or, alternatively, may be different software (loaded on the same or a different electronic device) that is configured to effect changes in such software utilized by a patient.

In at least some implementations, configuration details are stored at a server or other location and accessed or propagated by software running on one or more electronic devices.

Exemplary Methodologies

In one or more preferred methodologies, a first party pays for one or more electronic devices to be utilized in a healthcare environment by another party. For example, in an exemplary preferred methodology, a first entity pays for an electronic device to be provisioned with software configured in a manner similar to that described hereinabove, and provided to a healthcare environment or provider, and the electronic device is configured to include programming and/or advertising associated with a product, drug, or treatment offered by, or associated with, the first entity or a related entity.

Exemplary Security Measures

In one or more preferred implementations, an electronic device is equipped with an RFID system, or other tracking tag/transmitter or the like. Further, in at least some implementations, an electronic device, or system as described herein, is programmed with a means to identify patients only by secret PIN numbers, and/or the data encrypted, so that in the event an electronic device is stolen, or a patient explores the electronic device, and the encryption is defeated, patients' identities will be kept confidential, thus insuring patient confidentiality with the electronic device under all circumstances.

Targeted Advertising

In one or more preferred implementations, targeted advertising is delivered which comprises advertising about a particular product or service, delivered to a patient or user, designed to target a specific diagnosis or condition of the patient, or just to target a patient in general demographic terms by banner advertisements, video, audio, text, or any combination. In at least some preferred implementations, such targeted advertising includes coupons, discounts, co-promotions and available other benefits generated by software loaded on an electronic device, and delivered to the patient. Targeted advertising may be based upon identified conditions, or may be based upon seasonal conditions, such as summer based pollen allergies or winter cold and flu. It may also be based upon region or location information, for example advertisements for sunscreen might be provided in locations such as coastal communities year round. It could also be based upon a combination of seasonal and regional information, for example advertisements for sunscreen could be provided in mountain resort communities in the winter. In at least some implementations, the advertisement may be targeted only in that it is directed to a patron of a health care environment, and not be targeted in any other way based on any other information.

Remote Systems

In one or more preferred implementations, a system need not utilize an electronic device that resides in a health care provider's office. In at least some implementations, a health care provider advertises for and directs prospective patients to an offsite office, website, phone system or like means for communication. In such implementations, a computing device, cell phone, smart phone, or tablet is utilized by a patient, and a system is utilized to gather the necessary initial information from prospective patients electronically via phone, internet, or the like. After the data is collected and the prospective patient is informed, views, and/or listens to any provided information or advertisements (as described herein), he or she is referred to a participating health care provider and information is gathered from the patient, processed, and transmitted to the participating health care provider. The health care provider would then counsel the patient based on the provided data, and then the data would be transmitted back into the system for further processing and use (as described herein).

In one or more preferred implementations, a system is configured for automatic communication of a prescription to a pharmacy or other entity. In some preferred implementations, this will be a pharmacy previously chosen by a patient, e.g. via an electronic device.

Other Exemplary Embodiments and Implementations

One or more exemplary systems comprising electronic devices for capturing user data are described hereinabove. Generally, in one or more preferred embodiments in accordance with the present invention, a digital interactive system is utilized.

Figure 21:
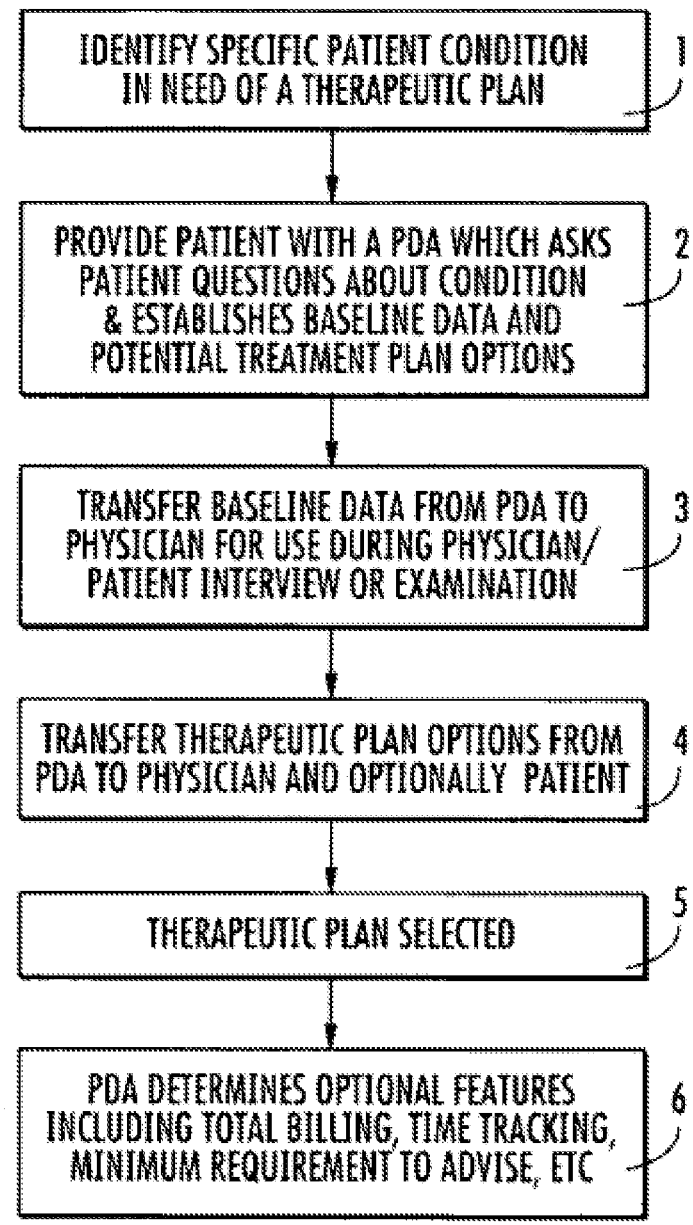
FIG. 21 is a flow diagram of a method in accordance with one or more embodiments of the present invention.

FIG. 21 is a flow diagram of a method in accordance with one or more embodiments of the present invention. When a patient arrives at a location for a physician exam or counseling (such as at a hospital, a physician's office, or a clinic), or initiates contact electronically (e.g., interacts with a physician through the internet), or the like, the patient will check in and the patient will be identified. During a patient triage, interview or examination, medical staff and/or the system itself preferably identifies a medical condition 1 in need of a therapeutic plan. This could be, for example, the treatment of smoking, alcohol or drug abuse, or any other type medical condition.

Once a particular medical condition is identified 1, then the patient is preferably provided with a digital interactive system. A digital interactive system may refer to a computer or computer like interface. Examples of digital interactive systems include tablets, smartphones, laptops, portable computers, PDAs, kiosks, cell phones, and the like, that have sufficient internal computing power, memory, and storage necessary, or can interact with an external computing device or source, e.g. an external server or a web site on the internet, to fulfill operations described herein. Generally, a digital interactive system represents a device (e.g. handheld, digital kiosk, etc.) that can ask questions, record the answers to the questions, and determine a therapeutic plan based on the input provided, regardless of whether the digital device accomplishes these steps directly or indirectly. For example, a digital interactive system could accomplish some of this utilizing a connection to a web site having such abilities, a cell phone could receive a downloaded e-mail or the like, or a PDA could receive a set of questions or have the questions on the device itself.

While in some preferred implementations a small mobile device like a tablet may be used, any type of device may be used, including a laptop, a computer kiosk or a custom designed handheld device. In some implementations, the device has one or more additional uses. The device can be a small handheld unit or can be a bigger handheld unit to enable the user to easily read any text on a display screen. In some preferred implementations, a screen size is generally 3 inches, 6 inches, 12 inches, or greater in some embodiments (e.g. in a kiosk).

The digital interactive system is preferably configured to query the patient with specific questions about the previously identified condition, and use that information to establish baseline data about the patient condition for which one or more potential therapeutic plans could be successfully utilized.

The baseline data is that information which enables a decision by the system to determine the best plan or plans for dealing with the patient medical condition, and the best or most appropriate targeted advertising. For example, in the case of a patient who wishes to stop smoking, the baseline data may be how frequent and how long the patient has been smoking, as well as how many cigarettes a day the patient smokes. Other important questions may relate to other types of cessation plans that have been tried, as well as particular allergies and the like. In a preferred implementations, the targeted advertisements are advertisements from companies that market smoking cessation products.

Once the system has established baseline data 2, the baseline data is transferred to the physician or other health care worker 3. In one embodiment, a digital device is merely handed to the healthcare worker to accomplish the transfer. However, the transfer of the baseline data can be accomplished in any convenient manner, such as, for example, by sending the information to a printer, to another computer, to the patient's file(s), or other such manner. The baseline data can be used by the physician to help counsel the patient, explain the particular medical condition and the like to the patient so that the physician can avoid the long process of obtaining that information himself, thus saving time and money in treating the patient.

In addition to the transfer of the baseline data from the digital interactive system, the digital interactive system will also transfer any therapeutic plan options it has determined viable to the physician 4 and targeted advertising to the patient. By sending the treatment options to the physician, the physician can make sure that all treatment possibilities are considered. In addition, where desirable, the patient can also view the therapeutic plan options and targeted advertising directly on the PDA which gives the physician the ability to work with an informed patient. Also, the treatment plan can, in some cases, be determined by both the physician and patient together, or even in some instances by the patient alone. In at least some implementations, the patient can view several videos, targeted advertising or other information on the digital device and use that information to make an informed choice. The digital interactive system could provide information to the physician and patient from the manufacturer of a plan, such as, for example, a pharmaceutical company, or the provider of a smoking cessation product. The information could be straight information or in the form of a targeted advertisement for the treatment plan to the patient, the physician or both. In addition, information gathered from the patient could be gathered for use in medical and marketing research. At the physician exam or consultation, the targeted advertising will have been viewed by the patient and the therapeutic plan can be selected 5 for or by the patient. In the case of prescription items the physician can then act accordingly and prescribe the appropriate therapeutic plan for the patient.

The digital device can, in some embodiments, have optional features. Those features might include billing functionality, general time tracking and the like. Other features might include writing and/or electronically sending prescriptions, helping the care provider analyze a patient's conditions, medications and allergies for potential negative interactions or improvements. In one embodiment, it can help identify a particular medication a patient is taking and has forgotten the name of by a series of questions.

Figure 22:
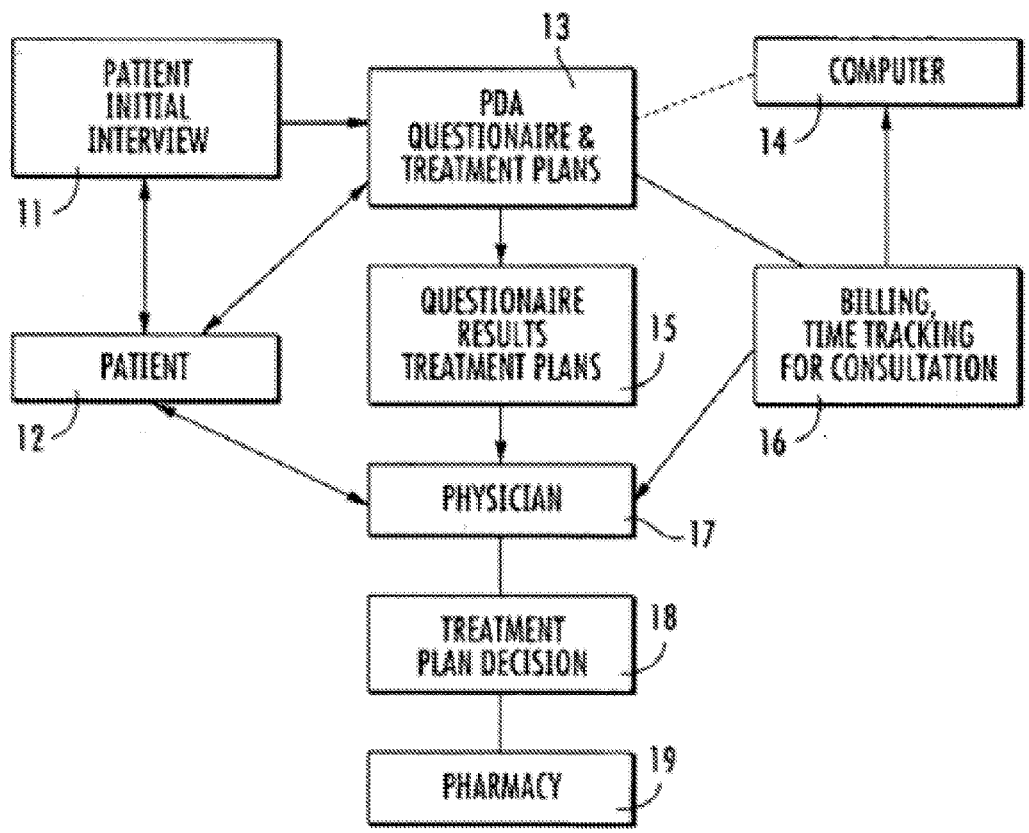
FIG. 22 is a diagram of an embodiment of a system in accordance with one or more embodiments of the present invention.

FIG. 22 is a diagram of an embodiment of a system in accordance with one or more embodiments of the present invention. A patient 12 goes to a physician's office, an admission desk, a clinic or the like and has a patient initial interview 11 with the triage or front desk or the like. At that event, the patient provides general information. For example, in an exemplary use case, at the initial triage the patient says they are a smoker. At that point, the initial interview 11 would have identified smoking as a medical condition. Other conditions could be similarly identified at the interview, such as drug use, negative or positive medication interaction, or the like.

For example, if another condition such as pregnancy is identified from the interview, a digital device could generate and present to a patient targeted advertisements for prescription products such as pre-natal vitamins and non-prescription products such as baby formula, bottles and diapers, and assist in obtaining third party benefits coverage for medical equipment, such as wheelchairs.

Following an interview, a patient 12 is given a digital device, such as a PDA, with a questionnaire 13 prior to consulting or examination by the physician that relates to the medical condition identified in the triage interview. The questions preferably are selected to obtain more detailed information about the condition and the answers to the questions preferably help identify one or more treatment plans 15 that could be used in the treatment of the medical condition. In addition, targeted advertisements could be provided to the patient at this point in time. Answers could be from any source. Questions could be specifically designed for the digital device or be questions developed by a third party provider specifically for deciding on a treatment plan. The questions could also be generated as a result of patient interaction and/or response to targeted advertising. Once the questionnaire 13 is completed the digital device uses that information to generate targeted advertising and formulate a treatment plan 15 or plans based on the most likely ones to match the needs and success of the particular patient.

In some preferred implementations, the digital device might query a patient regarding his or her insurance information, or his or her ability/willingness to pay for medication, and potential suggestions could be made to the patient regarding, coupons, discounts, eligibility for benefits, insurance tailoring insurance to their needs and smoking coverage resources for obtaining Medicare if eligible avoiding the "donut hole", etc.

Other questions could also be presented, such as: What pharmacy do you use?; Would you be willing to switch pharmacies, or use an online/home delivery option for all your medications?; Would receiving a valuable coupon make you want to switch pharmacies?; Would you like to review other medication choices that might work better for you rather than the current medications you receive?; Would you like a discounted membership for ABC Gym?; Would you like a coupon worth $10 off your first box of product X?; Did you know that Blue Cross/Blue Shield will pay for product X?; Did you know that as a member of AARP you are eligible for additional discounts on your medication?; Are you ever upset that your prescriptions are switched to less expensive generic versions without your consent?; or Would you like all your medications to be filled with the original name brand reliable medication? (conversely, the question could ask, "Would you like to save money by switching to these cheaper generic alternatives?").

Preferably, the questions are designed to: include highlighted therapeutic agents and exclude contraindications; generate targeted advertising; develop an appropriate secondary diagnosis relevant to, for example, smoking cessation counseling (e.g., emphysema) and billing; aid in marketing and therapeutic research; yield marketing data regarding a patient's choice of therapeutic agent; obtain and report back on health care providers prescribing patterns, especially as they relate to specific patient scenarios; collect data to help in research on how to improve quitting rates (or other therapeutic goals); help the patient fill out the appropriate paperwork to qualify for their medication being approved and paid for; and determine if there are additional benefits that they may qualify for under any third party plan in which they participate. The device is also useful in updating the patients list of medical conditions, history, medications and allergies, which may be used for targeted advertising on subsequent visits.

The device could also ask other questions of relevance during the question and answer period such as questions to document a patient's choice regarding potential therapeutic agents (e.g. John Doe requested a specific medication), and, on a subsequent visit, if a particular medication is already being used, questions designed to obtain marketing and research data as to why the choice was made, and how the patient is doing.

Once one or more treatment plans are decided upon the digital device can give information to the patient about them, which may include targeted advertising. It can merely list them, give detailed information about them, or in at least some implementations, provide videos or other presentations directly from the manufacturers of the particular treatment in the form of straight information or as a targeted advertisement. Once a patient is finished with the digital device, the information in the digital device about the patient can move in the system in a number of ways. One important thing the digital device can do is download the information to a computer 14. This can be an office computer, a server computer, a tablet, a PDA, the internet or the like, but in that way the information can be saved and transferred as needed by the physician and patient. The digital device can then provide results to the physician 17 on the treatment plans selected. This activity saves the physician the time to gather this information in a conference but still enables enough time to be spent to work on getting reimbursement for third party providers especially when that provider is the government which might require a certain amount of time to qualify for reimbursement. The physician 17 and patient 12 then can interact by way of consultation and or examination to come to a decision 18 on which of the available treatment plans will be selected. The patient can then go to the pharmacy 19 or other product provider to acquire the necessary product to accomplish the treatment plan.

Note that the digital device can also communicate with the computer and the system either the digital device 13 or the computer 14 can accomplish various other tasks 16. For example the digital device can track billing from the activity because it can track the time spent in "consultation" with the device.

Figure 23:
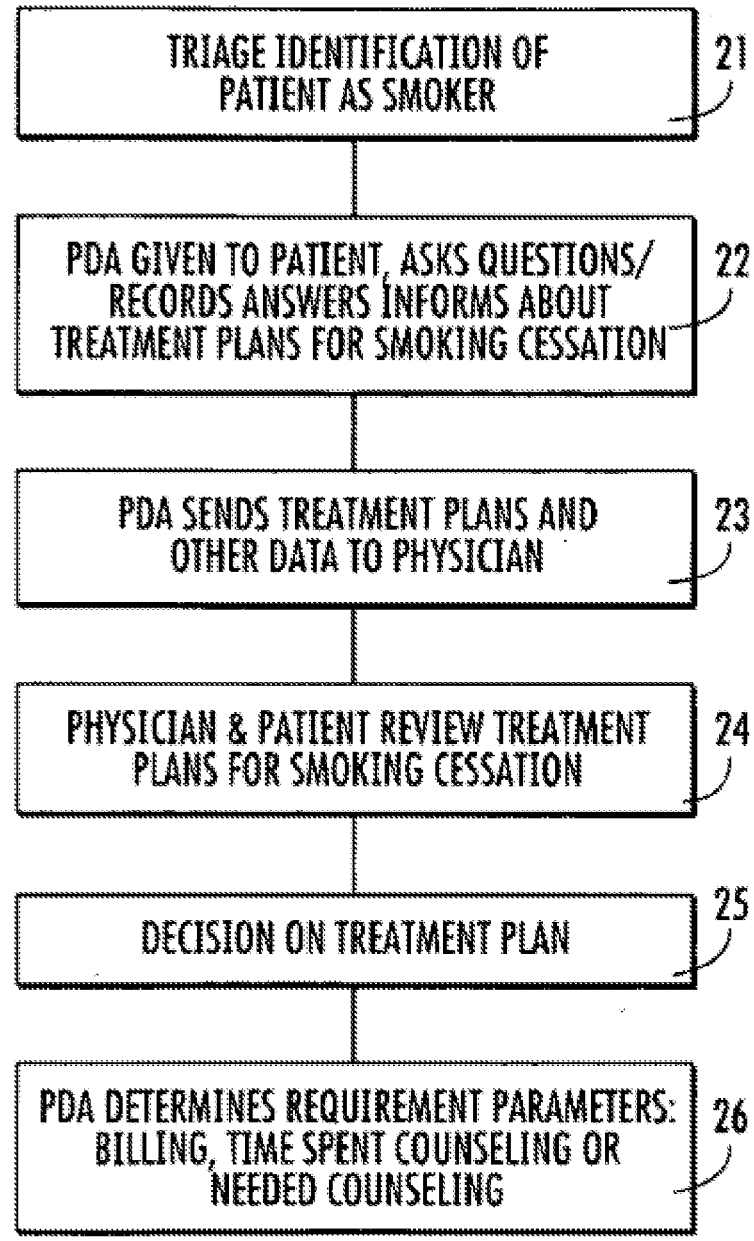
FIG. 23 details an exemplary use case relating to smoking cessation.

FIG. 23 details an exemplary use case relating to smoking cessation. As a patient enters a physician's office, a clinic or the like, a triage identifies a condition of the patient, whom in this example is a smoker 21. This can be accomplished by observation, by questionnaire, or the like. Once the patient is identified as having a smoking condition, a digital device is given to the patient 22 (alternatively, in some implementations, a user could use their own digital device and software or data could be delivered in any manner to their digital device). The digital device has questions programmed into it about the patient's smoking habits, and effects storage of the answers. The digital device then uses the answers to the questions to inform the patient with targeted advertising about the available treatment plans for cessation of smoking 22 that match the patient and his particular smoking problem. Note that this could be in the form of banner advertisements, coupons, text or video or the like format. The companies which produce the smoking cessation products could each have their own information to program into the PDA for viewing by the patient or the system could provide the information separately from commercially available information. In addition, particular brands of products could be emphasized by particular companies providing information for the PDA to give the patient. By working with pharmaceutical or other companies to highlight their products directly at the time treatment is offered, the companies have a higher likelihood of their product being selected when choice is an option.

Once the digital device has informed the patient about the smoking cessation options 22, the digital device can send the treatment plan and other related baseline data (the answers to the questions, targeted advertising preferences, etc for example) to the Physician 23. This could be done by sending the information to a printer, a different computer for viewing or the digital device itself could be used by the physician. In other embodiments the results of the digital device consultation are printed or otherwise placed on the patients chart.

With the results of the digital device consultation with the patient 22, the physician and patient can review the suggested or recommended treatment plans for the cessation of smoking. This can be a review of what the patient has already seen, and an opportunity to answer questions and discuss risks or whatever other information is necessary.

With the finishing of the discussion 25, the next step is to come to a decision on a treatment plan 26. This decision can be made by the physician, the patient or both in terms of which treatment plan would most likely be successful with the particular patient having noted the answers to the particular questionnaire.

The digital device is configured determine if third party benefits will pay for advertised products and will provide assistance in documentation for said benefits. The digital device preferably has other functionality as well, such as analyzing reimbursement requirements, facilitating billing to the patient or third party provider, tracking time spent in counseling, and recording of the process on the patient's chart either by printing the information out or transferring the information to the health care provider or health care provider's practice computer, or directly to the payor/billing company, etc.

Once a final decision is made and a particular product is purchased from a pharmacy, the digital device may also have the capability of sending the prescription to a given pharmacy of the physician or patient's choosing. Where cooperative pharmacies are involved, additional patient benefits may be obtained by using participating pharmacies.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. An electronic device comprising:
   (a) a processor;
   (b) a display screen; and
   (c) a non-transitory computer readable medium containing computer executable instructions configured to perform a method comprising
      (i) querying a user regarding a healthcare issue,
      (ii) providing, to the user via the display screen, information regarding a favored treatment for the healthcare issue,
      (iii) receiving, from the user, an indication of a preferred treatment,
      (iv) querying the user regarding information for calculating third party benefit information including household size information, insurance coverage information, and income information,
      (v) receiving from the user, in response to querying the user, information for calculating third party benefit information,
      (vi) automatically generating, using received household information, insurance coverage information, and income information, a recommendation as to where to apply for potential third party coverage of the preferred treatment, the computer executable instructions being configured to
         (A) determine, based on the received insurance coverage information, whether the user has certain benefit coverage, and proceed down a corresponding first decision branch based on such determination,
         (B) determine, based on the received household information, whether the user is single or a size of the patient's household, and proceed down a corresponding second decision branch based on such determination,
         (C) determine, based on the received income information, whether the user's income falls at or below a certain amount, and proceed down a third corresponding decision branch based on such determination, and
         (D) arrive at, based on having proceeded down the first, second, and third decision branches, the recommendation as to where to apply for potential third party coverage of the preferred treatment, and
      (vii) presenting the automatically generated recommendation as to where to apply for potential third party coverage of the preferred treatment.

2. The electronic device of claim 1, wherein the non-transitory computer readable medium contains computer executable instructions configured to generate one or more documents for printing.

3. The electronic device of claim 2, wherein the non-transitory computer readable medium contains computer executable instructions configured to automatically determine, based on information received from a patient and third party billing requirements, an amount of time to spend counseling the patient regarding the healthcare issue, and wherein the one or more documents include an indication of the determined amount of time to spend counseling the patient that was calculated based on third party billing requirements.

4. The electronic device of claim 2, wherein the one or more documents include an unsigned prescription for the preferred treatment of the patient.

5. The electronic device of claim 2, wherein the one or more documents include information regarding one or more disadvantages of the preferred treatment of the patient, the one or more disadvantages being identified based at least in part on information input by a patient via the electronic device.

6. The electronic device of claim 2, wherein the one or more documents include information regarding one or more advantages of the favored treatment.

7. The electronic device of claim 2, wherein the one or more documents include a checklist including information regarding counseling for the healthcare issue.

8. The electronic device of claim 2,
   (a) wherein the non-transitory computer readable medium of the base station contains computer executable instructions configured to perform a method comprising automatically determining, based on information received from a patient and third party billing requirements, an amount of time to spend counseling the patient regarding the healthcare issue;
   (b) wherein the one or more documents include an indication of the determined amount of time to spend counseling the patient that was calculated based on third party billing requirements;
   (c) wherein the one or more documents include an unsigned prescription for the preferred treatment of the patient;
   (d) wherein the one or more documents include information regarding one or more disadvantages of the preferred treatment of the patient, the one or more disadvantages being identified based at least in part on information input by a patient via the electronic device;
   (d) wherein the one or more documents include information regarding one or more advantages of the favored treatment; and
   (e) wherein the one or more documents include a checklist including information regarding counseling for the healthcare issue.

9. The electronic device of claim 1, wherein the electronic device comprises a tablet.

10. The electronic device of claim 1, wherein the electronic device comprises a phone.

11. The electronic device of claim 1, wherein the electronic device comprises a laptop.

12. The electronic device of claim 1, wherein the electronic device comprises a kiosk.

13. A system comprising:
    (a) a base station including
        (i) a processor, and
        (ii) a non-transitory computer readable medium; and
    (b) an electronic device including
        (i) a processor;
        (ii) a display screen; and
        (iii) a non-transitory computer readable medium containing computer executable instructions configured to perform a method comprising
            (A) querying a user regarding a healthcare issue,
            (B) providing, to the user via the display screen, information regarding a favored treatment for the healthcare issue,
            (C) receiving, from the user, an indication of a preferred treatment,
            (D) querying the user regarding information for calculating third party benefit information including household size information, insurance coverage information, and income information,
            (E) receiving from the user, in response to querying the user, information for calculating third party benefit information,
            (F) communicating patient information to the base station, the communicated patient information including the received household information, insurance coverage information, and income information,
            (G) receiving, from the base station in response to communicating the patient information, a recommendation as to where to where to apply for potential third party coverage of the preferred treatment, and
            (H) presenting the received recommendation as to where to apply for potential third party coverage of the preferred treatment;
    (c) wherein the non-transitory computer readable medium of the base station contains computer executable instructions configured to perform a method comprising
        (i) receiving patient information from the electronic device,
        (ii) automatically generating, using received household information, insurance coverage information, and income information, a recommendation as to where to apply for potential third party coverage of the preferred treatment, the computer executable instructions being configured to
            (A) determine, based on the received insurance coverage information, whether the user has certain benefit coverage, and proceed down a corresponding first decision branch based on such determination,
            (B) determine, based on the received household information, whether the user is single or a size of the patient's household, and proceed down a corresponding second decision branch based on such determination,
            (C) determine, based on the received income information, whether the user's income falls at or below a certain amount, and proceed down a corresponding third decision branch based on such determination, and
            (D) arrive at, based on having proceeded down the first, second, and third decision branches, the recommendation as to where to apply for potential third party coverage of the preferred treatment, and
        (iii) communicating the automatically generated recommendation to the mobile electronic device.

14. A system comprising:
    (a) a base station including
        (i) a processor, and
        (ii) a non-transitory computer readable medium; and
    (b) an electronic device including
        (i) a processor;
        (ii) a display screen; and
        (iii) a non-transitory computer readable medium containing computer executable instructions configured to perform a method comprising
            (A) querying a user regarding a healthcare issue,
            (B) providing, to the user via the display screen, information regarding a favored treatment for the healthcare issue,
            (C) receiving, from the user, an indication of a preferred treatment,
            (D) querying the user regarding information for calculating third party benefit information including household size information, insurance coverage information, and income information, (E) receiving from the user, in response to querying the user, information for calculating third party benefit information, (F) communicate patient information to the base station, the communicated patient information including the received household information, insurance coverage information, and income information;

(c) wherein the non-transitory computer readable medium of the base station contains computer executable instructions configured to perform a method comprising (i) receiving patient information from the electronic device, (ii) automatically generating, using received household information, insurance coverage information, and income information, a recommendation as to where to apply for potential third party coverage of the preferred treatment, the computer executable instructions being configured to (A) determine, based on the received insurance coverage information, whether the user has certain benefit coverage, and proceed down a corresponding first decision branch based on such determination, (B) determine, based on the received household information, whether the user is single or a size of the patient's household, and proceed down a corresponding second decision branch based on such determination, (C) determine, based on the received income information, whether the user's income falls at or below a certain amount, and proceed down a corresponding third decision branch based on such determination, and (D) arrive at, based on having proceeded down the first, second, and third decision branches, the recommendation as to where to apply for potential third party coverage of the preferred treatment, and (iii) effecting printing of one or more documents based on received patient information, (iv) wherein the one or more documents include an identification of the preferred treatment of the patient, and (v) wherein the one or more documents include an indication of the automatically generated recommendation.

15. The system of claim 14, wherein the non-transitory computer readable medium of the base station contains computer executable instructions configured to perform a method comprising automatically determining, based on information received from a patient and third party billing requirements, an amount of time to spend counseling the patient regarding the healthcare issue, and wherein the one or more documents include an indication of the determined amount of time to spend counseling the patient that was calculated based on third party billing requirements.

16. The system of claim 14, wherein the one or more documents include an unsigned prescription for the preferred treatment of the patient.

17. The system of claim 14, wherein the one or more documents include information regarding one or more disadvantages of the preferred treatment of the patient, the one or more disadvantages being identified based at least in part on information input by a patient via the electronic device.

18. The system of claim 14, wherein the one or more documents include information regarding one or more advantages of the favored treatment.

19. The system of claim 14, wherein the one or more documents include a checklist including information regarding counseling for the healthcare issue.

20. The system of claim 14, (a) wherein the non-transitory computer readable medium of the base station contains computer executable instructions configured to perform a method comprising automatically determining, based on information received from a patient and third party billing requirements, an amount of time to spend counseling the patient regarding the healthcare issue;

(b) wherein the one or more documents include an indication of the determined amount of time to spend counseling the patient that was calculated based on third party billing requirements;

(c) wherein the one or more documents include an unsigned prescription for the preferred treatment of the patient;

(d) wherein the one or more documents include information regarding one or more disadvantages of the preferred treatment of the patient, the one or more disadvantages being identified based at least in part on information input by a patient via the electronic device;

(d) wherein the one or more documents include information regarding one or more advantages of the favored treatment; and (e) wherein the one or more documents include a checklist including information regarding counseling for the healthcare issue.

* * * * *